United States Patent
Hosono et al.

(10) Patent No.: US 6,818,192 B2
(45) Date of Patent: Nov. 16, 2004

(54) 12CAO · 7AL$_2$O$_3$ COMPOUND CLATHRATING ACTIVE OXYGEN SPECIES AND METHOD FOR PREPARING THE SAME

(75) Inventors: Hideo Hosono, Yamato (JP); Masahiro Hirano, Tokyo (JP); Katsuro Hayashi, Kawasaki (JP)

(73) Assignee: Japan Science and Technology Corporation, Kawaguchi (JP)

( * ) Notice: Subject to any disclaimer, the term of this patent is extended or adjusted under 35 U.S.C. 154(b) by 332 days.

(21) Appl. No.: 09/926,765

(22) PCT Filed: Apr. 16, 2001

(86) PCT No.: PCT/JP01/03252

§ 371 (c)(1),
(2), (4) Date: Feb. 14, 2002

(87) PCT Pub. No.: WO01/79115

PCT Pub. Date: Oct. 25, 2001

(65) Prior Publication Data

US 2002/0172726 A1 Nov. 21, 2002

(30) Foreign Application Priority Data

Apr. 18, 2000 (JP) .................................... 2000-122368
Feb. 26, 2001 (JP) .................................... 2000-049524

(51) Int. Cl.$^7$ ........................... C01F 7/00; C01F 11/00; G01N 33/00; B01J 21/00; A01N 59/00
(52) U.S. Cl. .................. 423/115; 423/600; 73/19.01; 502/341; 424/688; 204/424; 429/27; 429/29; 429/33; 429/231.6
(58) Field of Search ................. 423/600, 115, 423/579; 73/19.01; 502/341; 424/688; 204/424; 429/27, 29, 33, 231.6

(56) References Cited

U.S. PATENT DOCUMENTS 5,908,713 A * 6/1999 Ruka et al. ............... 429/31

OTHER PUBLICATIONS

R. Stosser et al.; Journal of Solid State Chemistry 81, pp. 152–164, 1989, no month.

H. Hosono et al.; American Chemical Society, Inorganic Chemistry, vol. 26, No. 8, 1987, pp. 1192–1195, no month.

J. A. Imlach et al.; Cement and Concrete Research, vol. 1, pp. 57–61, 1971, no month.

J. H. Lunsford, Catalysis Review, 8 (1); pp. 135–157, 1973, no month.

M. Che; Advances in Catalysis, vol. 32, pp. 1–149, no date.

J. R. Brailsford et al.; The Journal of Chemical Physics, vol. 51, No. 11, pp. 4794–4798. Dec. 1969.

H. Hosono et al.; J. Am. Ceram. Soc. 70 (12) pp. 867–870, 1987, no month.

Von Hans Bartl et al.; N. Jahrbuch f. Mineralogie, Monatshefte 1970, pp. 547–552, no month.

* cited by examiner

*Primary Examiner*—Steven Bos
(74) *Attorney, Agent, or Firm*—Westerman, Hattori, Daniels & Adrian, LLP

(57) ABSTRACT

The present invention provides a 12CaO.7Al$_2$O$_3$ compound containing an O$_2^-$ ion radical and/or an O$^-$ ion radical in a high concentration of 10$^{20}$ cm$^{-3}$ or more. This compound can be used as an oxidization catalyst, antibacterial agent, ion conductor, or electrode material for solid-oxide fuel cells.

16 Claims, 3 Drawing Sheets

12CAO · 7AL$_2$O$_3$ COMPOUND CLATHRATING ACTIVE OXYGEN SPECIES AND METHOD FOR PREPARING THE SAME

TECHNICAL FIELD

The present invention relates to a 12CaO.7Al$_2$O$_3$ compound which is an oxide clathrating an O$_2^-$ ion radical and an O$^-$ ion radical as active oxygen species in a high concentration (hereinafter, these two ion radicals are referred collectively to as "active oxygen species"). The present invention also relates to a method for producing such a compound and to the use thereof.

BACKGROUND ART

An O$_2^-$ ion radical is known as one of active oxygen species which has a key role in oxidizing processes of various organic and inorganic materials. Extensive researches have heretofore been made on O$_2^-$ absorbed on the solid surface of an oxide compound (J. H. Lunsford, Catal, Rev. 8, 135, 1973, M. Che and A. J. Tench, Adv. Catal, 32, 1, 1983). In most of such researches, high-energy gamma rays are irradiated onto the surface of an oxide compound to create O$_2^-$ ion radicals thereon.

RO$_2$ (R:alkali metal) is known as a crystal including an O$_2^-$ ion radical as a constituent anion. However, the related compounds are unavailable for a certain application such as oxidation catalysts or ionic conductors, because all of the compounds will be readily decomposed even at a temperature of 300° C. or less.

As compared to O$_2^-$ ion radicals, O$^-$ ion radicals have higher activity. Several articles have reported that a small amount of O$^-$ ion radicals was included in alkali halide glasses, calcium-aluminosilicate glasses or the like (J. R. Bralsford et al., J. Chem. Physics, Vol. 49, pp 2237, 1968, H. Hosono et al., J. Am. Ceramic. Soc., 70, 867, 1987). However, there has not been known any crystal having an O$^-$ ion radical as a constituent ion.

In 1970, H. B. Bartl et al. made a point that among sixty-six oxygens within a unit cell containing two molecules in a 12CaO.7Al$_2$O$_3$ crystal, so-called C12A7, two oxygens of them existed within a space of each cage structure in the crystal as "free oxygens" without residing in a network of the crystal (H. B. Bartl and T. Scheller, Neuses Jarhrb. Mineral., Monatsh, 1970, 547).

Based on an electron spin resonance analysis, Hosono, one of the inventors, et al. have discovered that about 1×10$^{19}$ cm$^{-3}$ of O$_2^-$ was clathrated in a 12CaO.7Al$_2$O$_3$ crystal synthesized by reacting two raw materials, CaCO$_3$ and Al$_2$O$_3$ or CaCO$_3$ and Al (OH)$_2$, in a solid phase reaction at a temperature of 1200° C. in ambient atmosphere. They have proposed a model in which a part of free oxygens exists in each cage structure in the form of O$_2^-$ (H. Hosono and Y. Abe, Inorg. Che. 26, 1193, 1987).

12CaO.7Al$_2$O$_3$ is inherently a stable oxide having a melting point of 1415° C. If a larger amount of active oxygen species can be clathrated in this oxide and then a reversible incorporation and release of oxygen can be achieved, the oxide would have a desirable availability for various purposes, such as oxidation catalysts or ionic conductors.

While one of the inventors, et al. have found out that O$_2^-$ was clathrated in the 12CaO.7Al$_2$O$_3$ crystal, the concentration of O$_2^-$ was a relatively low value of 10$^{19}$ cm$^{-3}$ and any O$^-$ ion radical having higher activity has not been identified. Further, any effective technique for controlling the amount of O$_2^-$ and releasing/incorporating it from/into the crystal reversibly has not been achieved.

For using such a compound as high-efficiency oxidation catalysts or antibacterial agents, it is required to clathrate the active oxygen species in a higher concentration and to provide a reversible function for releasing the clathrated active oxygen species and incorporating oxygen from outside. It is also necessary to establish a technique for quantitatively analyzing the concentration of the clathrated active oxygen species.

DISCLOSURE OF INVENTION

The inventors have discovered that a 12CaO.7Al$_2$O$_3$ compound clathrating active oxygen species in a high concentration of 10$^{20}$ cm$^{-3}$ or more is obtained by preparing a raw material including calcium and aluminum mixed with each other in an atomic equivalent ratio of approximately 12:14 and then reacting the raw material in a solid phase reaction at a controlled temperature under a controlled atmosphere. The present invention is directed to such a compound itself, a method for producing the same, a method for releasing clathrated ions, and the use of the compound.

More specifically, the present invention provides a 12CaO.7Al$_2$O$_3$ compound produced by preparing a raw material including calcium and aluminum mixed with each other in an atomic equivalent ratio of approximately 12:14, preferably a raw material including calcium carbonate and gamma-aluminum oxide mixed with each other in a molecular equivalent ratio of approximately 12:7, and then reacting the raw material in a solid phase reaction at a sintering temperature of 1200° C. or more, preferably 1300° C., under an atmosphere with an oxygen partial pressure of 10$^4$ Pa or more and a water-vapor partial pressure of 10$^2$ Pa or less, preferably an oxygen partial pressure of 10$^5$ Pa or more and a water-vapor partial pressure of 1 Pa or less. This compound can include 10$^{20}$ cm$^{-3}$ or more of clathrated active oxygen species. The amount of the clathrated active oxygen species can be determined by an electron spin resonance analysis and a Raman spectrum analysis.

When the sintering atmosphere is arranged in an oxygen partial pressure less than of 10$^4$ Pa and a water-vapor partial pressure of more than 10$^2$ Pa, the concentration of the clathrated active oxygen species will be less than 10$^{20}$ cm$^{-3}$. Further, even under a dry oxidation atmosphere with an oxygen partial pressure of 10$^4$ Pa or more and a water-vapor partial pressure of 10$^2$ Pa or less, when the sintering temperature is arranged in less than 1200° C., it will be difficult to synthesize the desired 12CaO.7Al$_2$O$_3$ compound. Conversely, when the sintering temperature exceeds 1415° C., the raw material will be undesirably molten. Thus, it will also be hard to obtain the desired 12CaO.7Al$_2$O$_3$ compound. In case of synthesizing the 12CaO.7Al$_2$O$_3$ compound through a solid phase reaction, the mixture of calcium carbonate and gamma-aluminum oxide is suitable for the raw material. However, any combination of calcium hydroxide or calcium oxide and aluminum hydroxide or one of various aluminum oxides (alpha, gamma or theta aluminum oxide) may be used as the raw material to synthesize the above compound.

An electron spin resonance (ESR) spectrum (at 77 K) of the 12CaO.7Al$_2$O$_3$ compound clathrating the active oxygen species is formed of a superposition of two spectrums; one defined by gx=2.00, gy=2.01 and gz=2.04, the other defined by gx=gy=2.05 and gz=2.00. These g values correspond to those of $O_2^-$ ion radicals and $O^-$ ion radicals in the solid, respectively. Thus, it can be concluded that $O_2^-$ ion radicals and $O^-$ ion radicals are clathrated in the $12CaO.7Al_2O_3$ compound.

The absorption band shape in the ESR spectrum is symmetric at room temperature and becomes asymmetric at a low temperature of 77K. This indicates that $O_2^-$ ion radicals and $O^-$ ion radicals rotationally move within each cage structures at room temperature, while they are coupled electrostatically with and retained spatially by $Ca^{2+}$ ions residing on each wall of the cage structures at low temperature. Each concentration of $O_2^-$ ion radicals and $O^-$ ion radicals can be quantitatively determined from the intensity of the absorption band.

In a Raman scattering spectrum of the above compound, a strong scattering peak is exhibited around 1130 cm$^{-1}$. This peak corresponds to the peak of $O_2^-$ ion radicals which has been reported by K. Nakamoto et al. (K. Nakamoto, Infrared and Raman Spectra of Inorganic and Coordination Compound, 1978, Wiley). Since there is a certain dependence between the ESR absorption band and the Raman scattering intensity, the intensity of clathrated $O_2^-$ ion radicals can be quantitatively determined from the Raman scattering intensity. When the above compound is heated at 1200° C. or more under an oxygen partial pressure of 10$^4$ Pa or less or a water-vapor partial pressure of 10$^2$ Pa or more, the active oxygen species or oxygen molecules will be released from the compound.

BEST MODE FOR CARRYING OUT THE INVENTION

Figure 1:
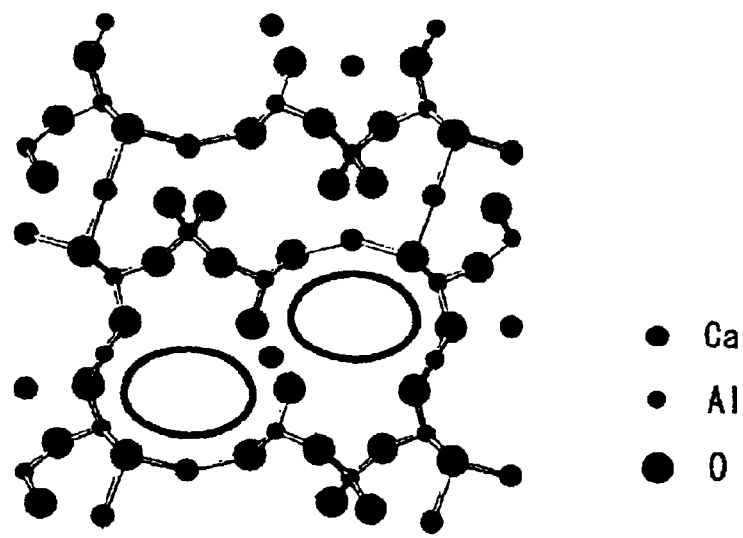
FIG. 1 is a schematic diagram showing the crystal structure of $12CaO.7Al_2O_3$.

As shown in FIG. 1, $12CaO.7Al_2O_3$ has a cubic crystal system with the space group 143d, and 2 molecules of $12CaO.7Al_2O_3$ exist in each unit lattice or unit cell of the crystal. $12CaO.7Al_2O_3$ has a melting point of 1415° C. The crystal has a structure in which $Ca^{2-}$ ions are located on a network structure formed of polymerized tetrahedrons of $AlO_4$. Each crystal lattice defines a space (cage) therewithin That is, 2 $(12CaO.7Al_2O_3)=Ca_{24}Al_{28}O_{66}=[Ca_{24}Al_{28}O_{64}]^{4+}.2O^{2-}$. The $O^{2-}$ is referred to as a free oxygen, which exists within the cage. Generally, the $O^{2-}$ is coordinated by a cation all the time and thereby hardly to be free. However, in the $12CaO.7Al_2O_3$ crystal, the $O_2^-$ ion resides within the cage. Thus, the $O^{2-}$ ion can be free without coupling with the cation. This state is referred to as "calthration". In this state, the $O^{2-}$ ion is chemically active as in the state when absorbed on a solid surface.

The $O^{2-}$ ion clathrated by the cage is confined within the cage so as to prevent any reaction with the outside atmosphere. However, in a high temperature of 1200° C. or more, the size of the cage is thermally expanded. This allows oxygen molecules from the atmosphere to pass through the bottleneck of the cage. Consequently, the following reaction will be caused.

$O^{2-}$ (within the cage)+$O_2$ (from the atmosphere)=$O^-$ (within the cage)+$O_2^-$ (within the cage)

Thus, a pair of $O^-$ and $O_2^-$ is generated from an oxygen ion $O^{2-}$ residing in each of the unit cell as a result of the reaction with $O_2$ molecule. The $12CaO.7Al_2O_3$ compound clathrating $O^-$ and $O_2^-$ in a high concentration can be represented by 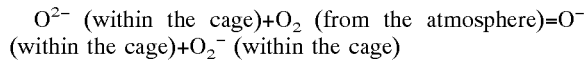, where m≦2, and the $O_2^-$ and $O^{2-}$ are clathrated within the cage.

By subjecting the compound to a heat treatment at a temperature of 1200° C. or more under an atmosphere with an oxygen partial pressure of 10$^4$ Pa or less or a water-vapor partial pressure of 10$^2$ Pa or more, oxygen molecules from the atmosphere actively pass through the bottleneck of the cage. Thus, during the course of the transition of the concentration of the active oxygen ion radicals to a certain equilibrium concentration, the active oxygen ion radicals can be released from the cage to the atmosphere.

The $O_2^-$ ion radicals clathrated in the $12CaO.7Al_2O_3$ compound of the present invention can be quantitatively analyzed through the use of a scattering intensity caused by the $O_2^-$ ion radicals around a Raman shift of 1128 cm$^{-1}$.

The $O_2^-$ ion radicals and the $O^-$ ion radicals each clathrated in the $12CaO.7Al_2O_3$ compound can also be quantitatively analyzed through the use of two electron spin resonance absorption intensities; one defined by gx=2.00, gy=2.01 and gz=2.04, the other defined by gx=gy=2.05 and gz=2.00.

EXAMPLE

The present invention will be more specifically described in connection with inventive examples and a comparative example.

Inventive Example 1

A powder of raw material including calcium carbonate and gamma-alumina mixed with each other in a molecular equivalent ratio of 12:7 was sintered at 1300° C. under an atmosphere with an oxygen partial pressure of 1 Atm (10$^{-1}$ MPa) for two hours (sample 1). Through an X-ray diffraction analysis, the obtained sample 1 was verified as a $12CaO.7Al_2O_3$ compound. An ESR spectrum of the obtained compound was measured at each of room temperature and 77K.

Figure 2:
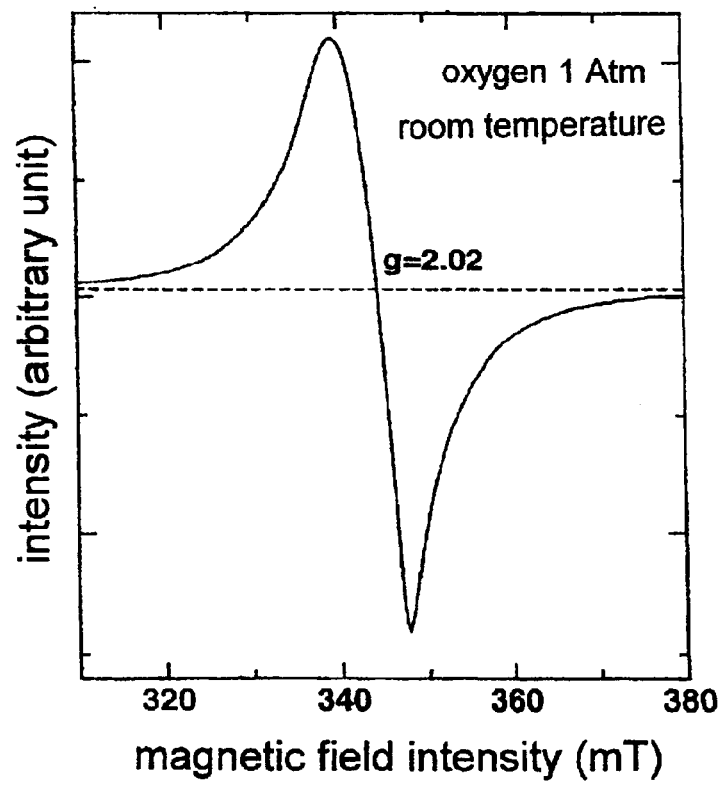
FIG. 2 is a graph showing an ESR spectrum of a compound obtained in an inventive example 1, at room temperature.
Figure 3:
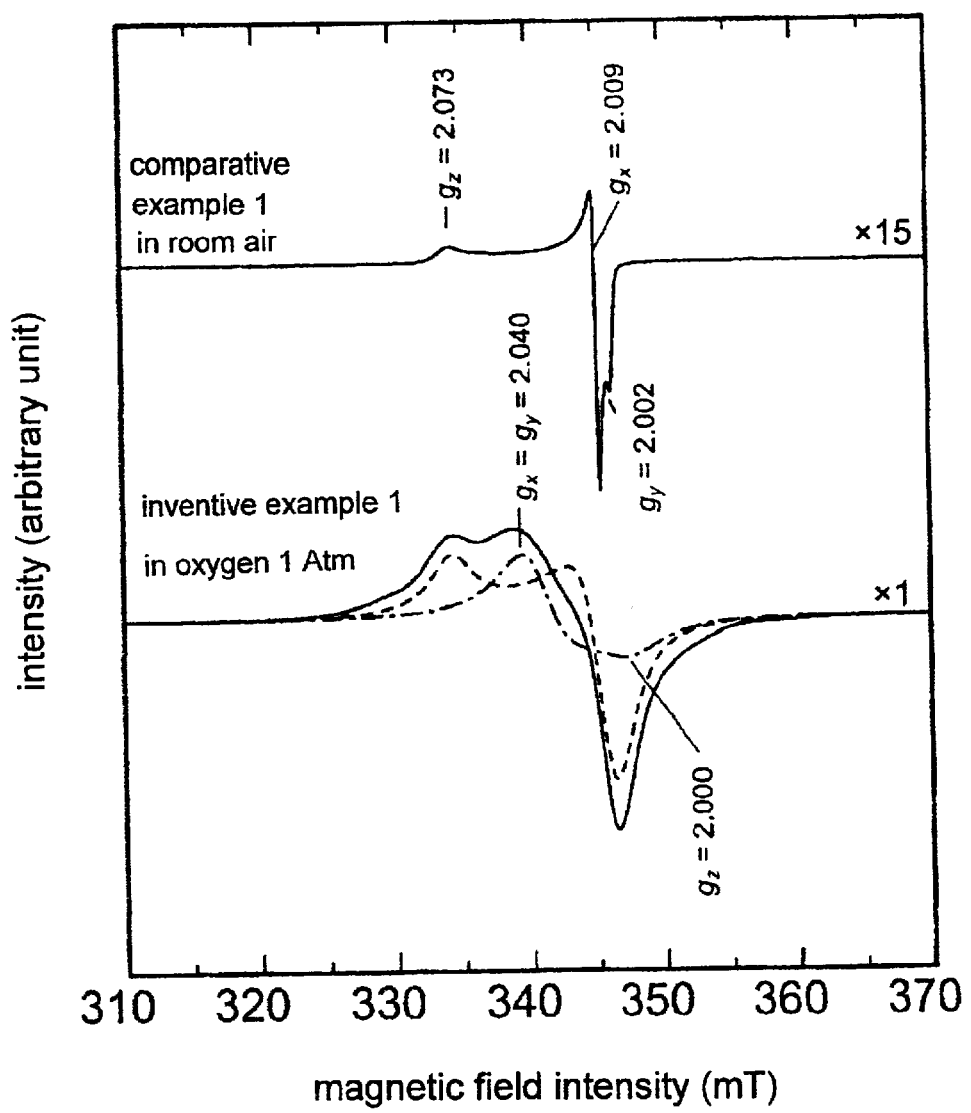
FIG. 3 is a graph showing an ESR spectrum (at 77K) of each compound obtained in the inventive example 1 and a comparative example 1.

FIGS. 2 and 3 show ESR spectra of the obtained compound of the example 1 measured at room temperature and 77K, respectively. The wavelength of microwave used was 9.75 GHz. At room temperature, an absorption band having a symmetric shape with respect to a magnetic field intensity of 343 mT was observed. The g value was determined as 2.02. At 77K, an asymmetric absorption band was observed. Each of these absorption bands was formed of a superposition of one absorption band defined by gx=2.002, gy=2.009 and gz=2.073 arising from $O_2^-$ ion radicals, and another absorption band defined by gx=gy=2.042 and gz=2.001 arising from $O^-$ ion radicals. Each concentration of the $O_2^-$ ion radicals and the $O^-$ ion radicals is quantitatively determined as 1×10$^{21}$ cm$^{-3}$ from respective intensities of the absorption bands.

Comparative Example 1

A powder of raw material including calcium carbonate and gamma-alumina mixed with each other in a molecular equivalent ratio of 12:7 was sintered at 1300° C. in air (oxygen partial pressure of ($2 \times 10^4$ Pa, water-vapor partial pressure of more than $10^2$ Pa)for two hours (sample 2 or comparative example 1). Through an X-ray diffraction analysis, the obtained sample 2 was verified as a $12CaO.7Al_2O_3$ compound. FIG. 3 shows an ESR spectrum at 77K. In the comparative example 1 (sample 2), an absorption band is divided into three components, which are determined as gx=2.009, gy=2.002 and gz=2.073, respectively. This absorption band is caused by $O_2^-$ ion radicals, and the concentration of the $O_2^-$ ion radicals is quantitatively determined as $1 \times 10^{19}$ cm$^{-3}$.

Figure 4:
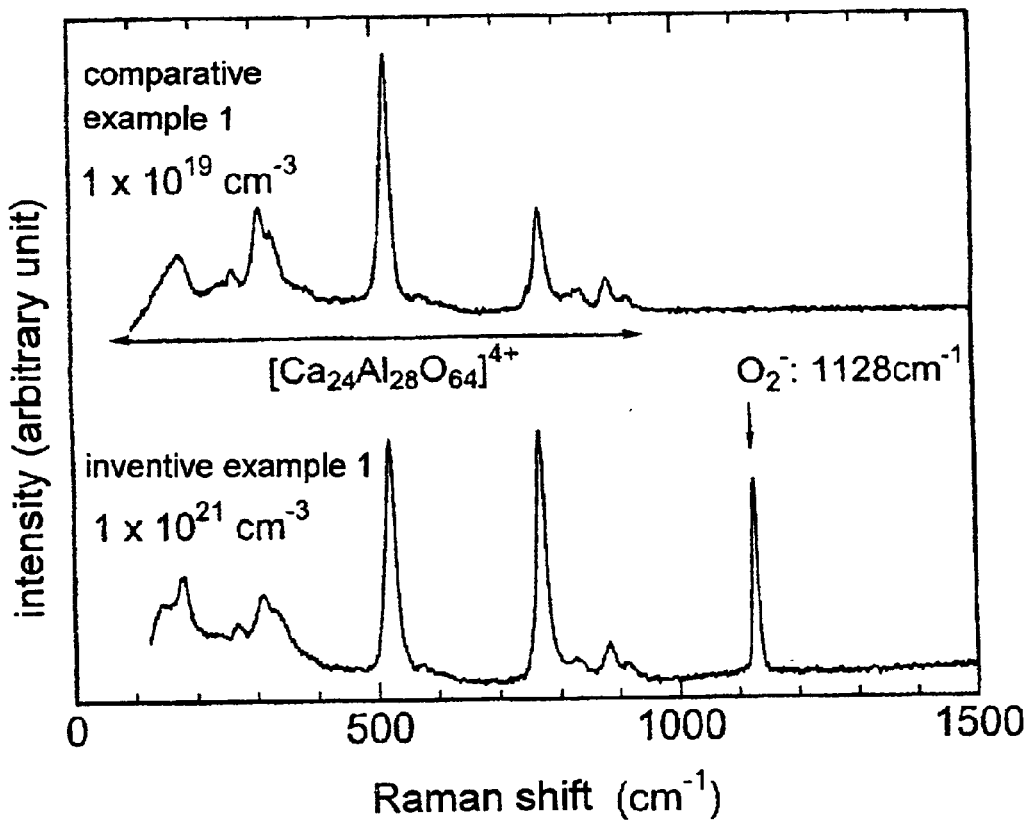
FIG. 4 is a graph showing each Raman spectrum of the compounds obtained in the inventive example 1 and the comparative example 1.

A Raman spectrum was measured for each of the inventive example 1 (sample 1) and the comparative example 1 (sample 2). FIG. 4 shows the Raman spectra obtained from the inventive example 1 and the comparative example 1. In both the spectra, several scattering lines arising from $[Ca_{24}Al_{28}O_{64}]^{4+}$ were observed in the energy range of 1000 cm$^{-1}$ or less. In the inventive example 1 (sample 1), an additional Raman peak arising from the $O_2^-$ ion radicals was observed at a Raman shift of 1128 cm$^{-1}$.

Inventive Example 2

A powder of raw material including calcium carbonate and gamma-alumina mixed with each other in a molecular equivalent ratio of 12:7 was sintered at 1300° C. in room air for two hours (sample 1), and then additionally annealed at 1300° C. under an atmosphere with an oxygen partial pressure of 1 Atm ($10^{-1}$ MPa) for two hours (sample 3). Through an X-ray diffraction analysis, the obtained sample 3 was verified as a $12CaO.7Al_2O_3$ compound. The concentration of $O_2^-$ ion radicals included in the obtained $12CaO.7Al_2O_3$ compound was quantitatively determined from ESR and Raman-scattering spectra. The determined amount of the clathrated $O_2^-$ ion radicals was $1 \times 10^{21}$ cm$^{-3}$. From the ESR spectrum, it was also proved that $O^-$ ion radicals were clathrated by a concentration of $1 \times 10^{21}$ cm$^{-3}$.

Inventive Example 3

The $12CaO.7Al_2O_3$ compound obtained from the inventive example 1 was subjected to a heat treatment at 1300° C. in air (oxygen partial pressure of $2 \times 10^4$ Pa, water-vapor partial pressure of more than $10^2$ Pa) for two hours (sample 4). The concentration of $O_2^-$ ion radicals included in the $12CaO.7Al_2O_3$ compound after the heat treatment was quantitatively determined from ESR and Raman-scattering spectra. The determined amount of the clathrated $O_2^-$ ion radicals was $1 \times 10^{19}$ cm$^{-3}$. It is proved that the active oxygen species have been reduced by 3.8−0.02=3.78 for each of the unit cell through the heat treatment. Most of these active oxygen species were released to the atmosphere.

Figure 5:
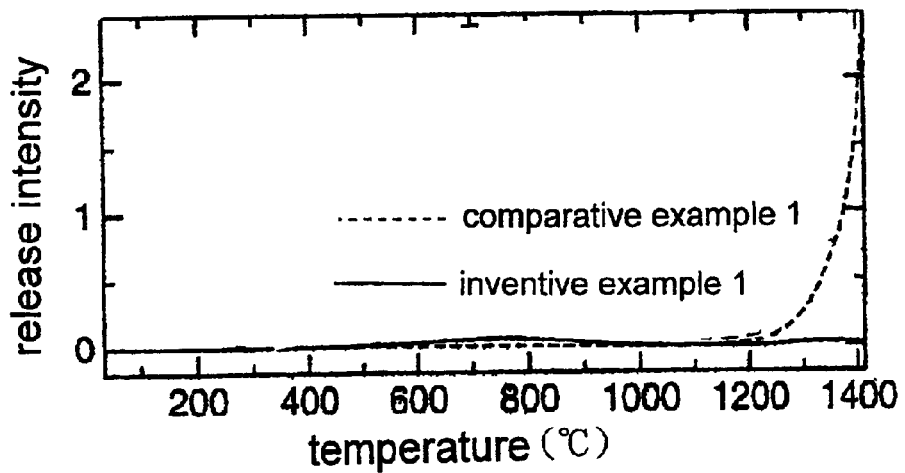
FIG. 5 is a graph showing an analytical curve of temperature to release-gas intensity with a molecular mass/charge ratio=32 in each of the $12CaO.7Al_2O_3$ compounds obtained in the inventive example 1 and comparative example 1.

The $12CaO.7Al_2O_3$ compound obtained from the inventive example 1 was subjected to an analysis for determining a release-gas intensity with increasing temperature. The measurement was done in a vacuum atmosphere. It was confirmed that the obtained compound of the inventive example 1 exhibited a sharply rising peak with a molecular mass/charge ratio=32, and the active oxygen species were released from the compound. FIG. 5 shows an analytical curve of temperature to release-gas intensity with a molecular mass/charge ratio=32 in each of the $12CaO.7Al_2O_3$ compounds obtained from the inventive example 1 and comparative example 1.

Concentrations of the active oxygens in the inventive examples and the comparative example will be shown in Table 1.

TABLE 1

|  | Conditions of Burning and heating | concentration of $O_2^-$ ion radical (cm$^{-3}$) (per unit cell) | concentration of $O^-$ ion radical (cm$^{-3}$) (per unit cell) |
| --- | --- | --- | --- |
| Inventive Example 1 | In oxygen 1 Atm 1300° C., two hours | $1 \times 10^{21}$/1.9 | $1 \times 10^{21}$/1.9 |
| Inventive Example 2 | In air 1300° C., two hours + In oxygen 1 Atm 1300° C., two hours | $1 \times 10^{21}$/1.9 | $1 \times 10^{21}$/1.9 |
| Inventive Example 3 | In oxygen 1 Atm 1300° C., two hours + In air 1300° C., two hours | $1 \times 10^{19}$/0.02 | below sensitivity limits/ below sensitivity limits |
| Comparative Example 1 | In air 1300° C., two hours | $1 \times 10^{19}$/0.02 | below sensitivity limits/ below sensitivity limits |

The amount of active oxygen species clathrated in each of the inventive example 1 (sample 1) and the inventive example 2 (sample 3) is 3.8 per unit cell. This value is almost equal to the theoretically calculated maximum total value of 2+2=4.

As shown the above examples, clathrated active oxygen species and incorporating oxygen from the atmosphere can be achieved by controlling the temperature and the oxygen partial pressure of the atmosphere during the sintering process of $12CaO.7Al_2O_3$, and releasing of the clathrated active oxygen species can be achieved by the heat treatment of the obtained $12CaO.7Al_2O_3$ compound under the controlled oxygen partial pressure of the atmosphere.

INDUSTRIAL APPLICABILITY

The present invention provides a $12CaO.7Al_2O_3$ compound which clathrates active oxygen species in a high concentration of $10^{20}$ cm$^{-3}$ or more and allows the clathrated active oxygen species or oxygen ions to be released at a high temperature of 1250° C. or more. Thus, this compound can be used as an oxidization catalyst, for example, in order to oxidize organic materials. Further, the active oxygen species has an excellent antibacterial action as is generally known. Thus, the $12CaO.7Al_2O_3$ compound clathrating a large amount of active oxygen species according to the present invention can also be used as an effective antibacterial agent.

Furthermore, the active oxygen species in the $12CaO.7Al_2O_3$ compound clathrating a large amount of them can substantially freely move within the crystal structure. This opens the way for applying the $12CaO \cdot 7Al_2O_3$ compound of the present invention to an ion conductor. Moreover, by combining the ion conductivity with the ability of oxidizing organic materials, this compound can be used as an electrode material for solid-oxide fuel cells.

What is claimed is:

1. A $12CaO \cdot 7Al_2O_3$ compound comprising an $O_2^-$ ion radical and/or an $O^-$ ion radical serving as active oxygen species, said ion radical being clathrated in said compound in a concentration of $10^{20}$ cm$^{-3}$ or more.

2. A method for producing a $12CaO \cdot 7Al_2O_3$ compound comprising the steps of:

preparing a raw material powder including calcium (Ca) and aluminum (Al) mixed with each other in an atomic equivalent ratio of 12:14; and reacting said raw material in a solid phase reaction at a sintering temperature ranging between 1200° C. or more and less than 1415° C., under a dry oxidization atmosphere with an oxygen partial pressure of $10^4$ Pa or more and a water-vapor partial pressure of $10^2$ Pa or less.

3. A method as defined in claim 2, wherein said raw material includes a calcium component selected from the group consisting of calcium carbonate, calcium hydroxide and calcium oxide, and an aluminum component selected from the group consisting of aluminum oxide and aluminum hydroxide.

4. A method for releasing an active oxygen species clathrated in the $12CaO \cdot 7Al_2O_3$ compound as defined in claim 1, characterized by subjecting said $12CaO \cdot 7Al_2O_3$ compound to a heat treatment at a temperature of 1200° C. or more under an atmosphere with an oxygen partial pressure of less than $10^4$ Pa or a water-vapor partial pressure of more than $10^2$ Pa.

5. A method for quantitatively analyzing the $O_2^-$ ion radical clathrated in the $12CaO \cdot 7Al_2O_3$ compound as defined in claim 1, characterized in that an amount of said $O_2^-$ ion radical is measured based on a scattering intensity arising from said $O_2^-$ ion radical around a Raman shift of 1128 cm$^{-1}$.

6. A method for quantitatively analyzing the $O_2^-$ ion radical and $O^-$ ion radical each clathrated in the $12CaO \cdot 7Al_2O_3$ compound as defined in claim 1, characterized in that amounts of said $O_2^-$ ion radical and said $O^-$ ion radical are measured based on a first electron spin resonance absorption intensity defined by $gx=2.00$, $gy=2.01$ and $gz=2.04$, and a second electron spin resonance absorption intensity defined by $gx=gy=2.05$ and $gz=2.00$, respectively.

7. An oxidization catalyst comprising a $12CaO \cdot 7Al_2O_3$ compound including an $O_2^-$ ion radical and/or an $O^-$ ion radical serving as active oxygen species, said ion radical being clathrated in said compound in a concentration of $10^{20}$ cm$^{-3}$ or more.

8. An antibacterial agent comprising a $12CaO \cdot 7Al_2O_3$ compound including an $O_2^-$ ion radical and/or an $O^-$ ion radical serving as active oxygen species, said ion radical being clathrated in said compound in a concentration of $10^{20}$ cm$^{-3}$ or more.

9. An ion conductor comprising a $12CaO \cdot 7Al_2O_3$ compound including an $O_2^-$ ion radical and/or an $O^-$ ion radical serving as active oxygen species, said ion radical being clathrated in said compound in a concentration of $10^{20}$ cm$^{-3}$ or more.

10. An electrode material for solid-oxide fuel cells, comprising a $12CaO \cdot 7Al_2O_3$ compound including an $O_2^-$ ion radical and/or an $O^-$ ion radical serving as active oxygen species, said ion radical being clathrated in said compound in a concentration of $10^{20}$ cm$^{-3}$ or more.

11. A compound, as defined in claim 1, comprising an $O^-$ ion radical in a concentration of $10^{20}$ cm$^{-3}$ or more.

12. An oxidization catalyst, as defined in claim 7, wherein said $12CaO \cdot 7Al_2O_3$ compound includes an $O^-$ ion radical in a concentration of $10^{20}$ cm$^{-3}$ or more.

13. An antibacterial agent, as defined in claim 8, wherein said $12CaO \cdot 7Al_2O_3$ compound includes an $O^-$ ion radical in a concentration of $10^{20}$ cm$^{-3}$ or more.

14. An ion conductor, as defined in claim 9, wherein said $12CaO \cdot 7Al_2O_3$ compound includes an $O^-$ ion radical in a concentration of $10^{20}$ cm$^{-3}$ or more.

15. An electrode material, as defined in claim 10, wherein said $12CaO \cdot 7Al_2O_3$ compound includes an $O^-$ ion radical in a concentration of $10^{20}$ cm$^{-3}$ or more.

16. A compound, as defined in claim 1, wherein said ion radical is clathrated in said compound in a concentration of $10^{20}$ cm$^{-3}$ or more during the synthesis of said compound by sintering a raw material powder including calcium (Ca) and aluminum (Al) mixed with each other in a solid phase reaction.

* * * * *